(12) United States Patent
Hildbrand et al.

(10) Patent No.: US 7,910,728 B2
(45) Date of Patent: Mar. 22, 2011

(54) PROCESS FOR THE PREPARATION OF A MACROCYCLE

(75) Inventors: Stefan Hildbrand, Moehlin (CH); Kurt Puentener, Basel (CH); Michelangelo Scalone, Birsfelden (CH)

(73) Assignee: Roche Palo Alto LLC, South San Francisco, CA (US)

( * ) Notice: Subject to any disclaimer, the term of this patent is extended or adjusted under 35 U.S.C. 154(b) by 208 days.

(21) Appl. No.: 12/317,116

(22) Filed: Dec. 19, 2008

(65) Prior Publication Data

US 2009/0163706 A1   Jun. 25, 2009

(30) Foreign Application Priority Data

Dec. 21, 2007   (EP) .................................... 07150287

(51) Int. Cl.
C07D 519/00   (2006.01)

(52) U.S. Cl. ...................................................... 540/460
(58) Field of Classification Search .................. 540/460
See application file for complete search history.

(56) References Cited

U.S. PATENT DOCUMENTS

2007/0054842 A1   3/2007   Blatt et al.

FOREIGN PATENT DOCUMENTS

| EP | 1825913 A1 | 2/2007 |
|---|---|---|
| WO | 02083742 A2 | 10/2002 |
| WO | 2005016944 A1 | 2/2005 |
| WO | WO 2005/037214 A2 | 4/2005 |
| WO | 2006043145 A1 | 4/2006 |
| WO | 2007140954 A1 | 12/2007 |
| WO | 2008086161 A1 | 7/2008 |

OTHER PUBLICATIONS

Furstner, A., "Olefin Methathesis and Beyond," Angewandte Chemie International Edition, 2000, vol. 39 (17), pp. 3012-3043.
Tsantrizos, Y. S., et. al. "Olefin ring-closing methathesis as a powerful tool in drug discovery and development -potent macrocyclic inhibitors of the hepatitis C virus NS protease," Journal of Organometallic Chemistry, 2006, vol. 691 (24-25), pp. 5163-5171.
Yee, N. K., et. al. "Efficient Large-Scale Synthesis of BILN 2061, a Potent HCV Protease Inhibitor, by a Convergent Approach Based on Ring-Closing Methathesis," The Journal of Organic Chemistry, 2006, vol. 71 (19), pp. 7133-7145.

*Primary Examiner* — Bruck Kifle
(74) *Attorney, Agent, or Firm* — Brian L. Buckwalter

(57) ABSTRACT

The present invention relates to a new process for the preparation o macrocyclic HCV protease inhibitor compounds of the formula

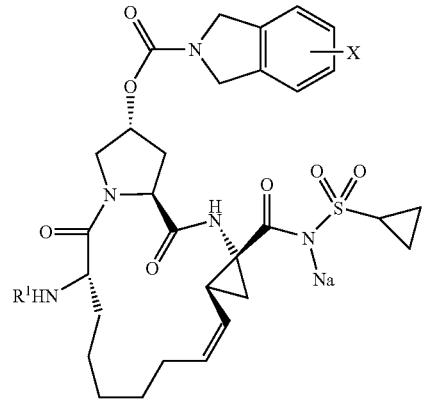

wherein $R^1$ is an amino protecting group and X is halogen by way of a ring closing metathesis approach.

13 Claims, No Drawings

PROCESS FOR THE PREPARATION OF A MACROCYCLE

CROSS REFERENCE TO PRIOR APPLICATIONS

This application claims the benefit of priority to EP 07150287.6 filed Dec. 21, 2007 the contents of which is hereby incorporated in their entirety by reference.

FIELD OF THE INVENTION

The present invention relates to identification an improved process for the preparation of the macrocyclic lactam of formula I which is a useful intermediate for the large scale manufacture of VII. Compounds of formula VII are inhibitors of HCV protease and are useful for treating HCV infections.

BACKGROUND OF THE INVENTION

Macrocyclic lactams of general formula VII wherein $R^1$ is an amino protecting group and X is halogen. and particularly of formula VIII have been found to be potent inhibitors of HCV protease. Compound VIII is currently in preclinical development.

The key step in one synthesis of the macrocyclic compounds of formula VII is a ring closing metathesis (RCM) reaction of a diene compound in the presence of a suitable ring closing metathesis catalyst. PC Publication WO 2005/037214 or PCT Publication

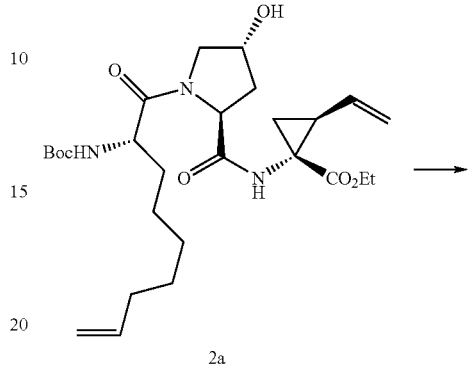

2a

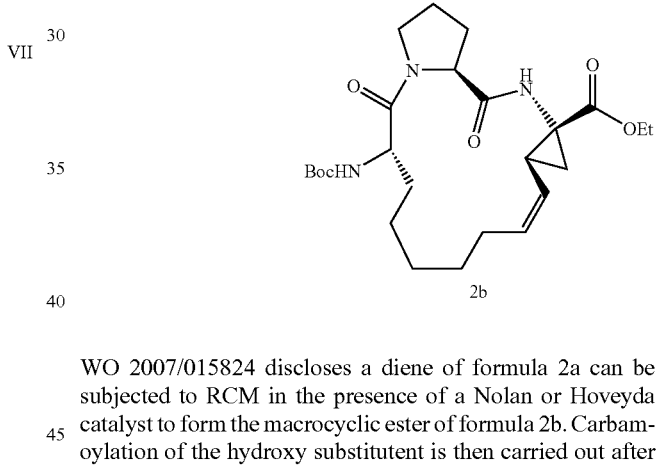

2b

WO 2007/015824 discloses a diene of formula 2a can be subjected to RCM in the presence of a Nolan or Hoveyda catalyst to form the macrocyclic ester of formula 2b. Carbamoylation of the hydroxy substitutent is then carried out after the ring closure. Unfortunately the RCM as disclosed in the art suffers from modest yields and low catalyst selectivity, which translate into low efficiency and high costs.

There is a need for an improved process which is applicable on technical scale and which overcomes the limitations of the processes disclosed in the prior art.

SUMMARY OF THE INVENTION

The present invention provides a process for the manufacture of a compounds according to formula I or VII. Compound I is a useful intermediate useful intermediates for the preparation of VII which is an inhibitor of HCV protease.

The invention provides process comprising the step of contacting a diene of formula II wherein $R^1$ is an amino protecting group, $R^2$ is $C_{1-4}$-alkyl and X is a halogen atom with a penta-coordinated ruthenium (II) carbene complex to manufacture of a macrocyclic compound of formula I which can be converted to a medicament of formula VII.

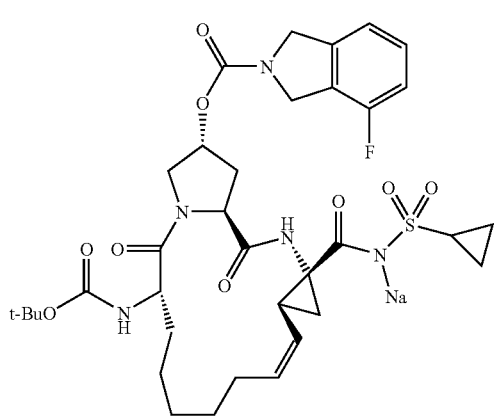

VII

VIII

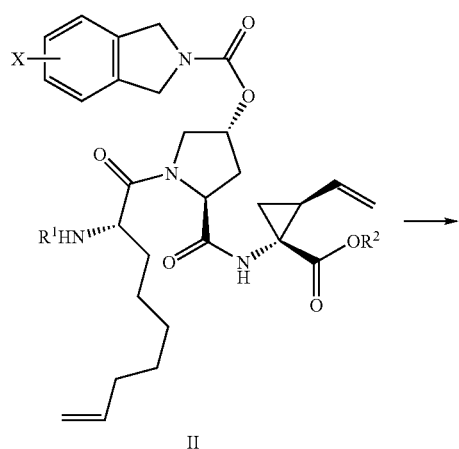

II

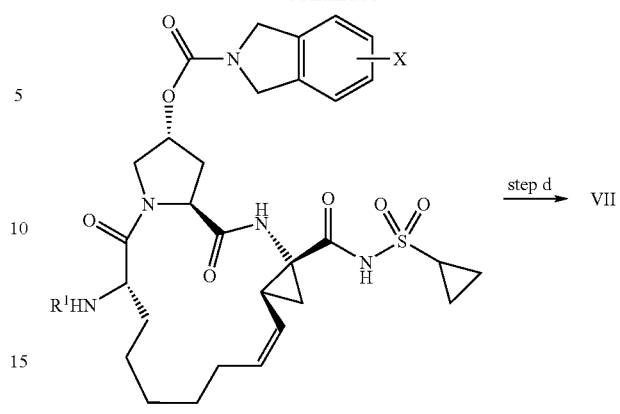

XXI

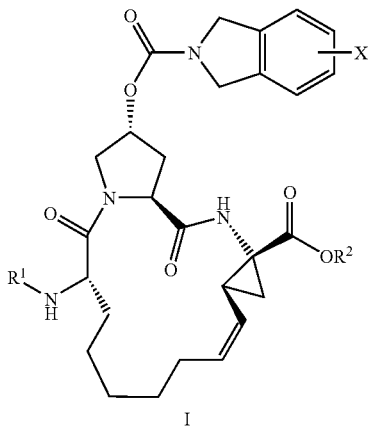

I

The invention further provides a method for the preparation of a medicament of formula I which further comprises the steps of hydrolyzing the ester (step b), forming the acyl sulfonamide (step c) and conversion of the acyl sulfonamide XXI to a salt.

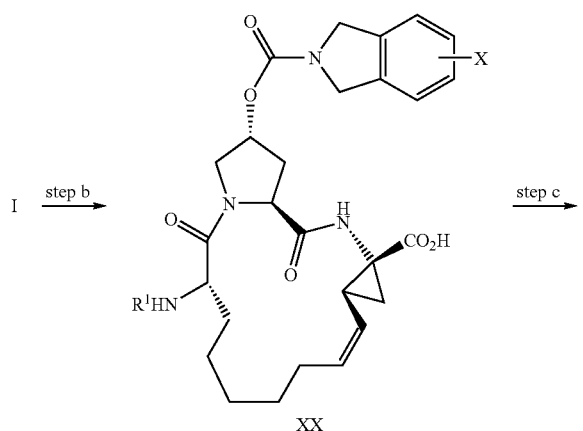

XX

DETAILED DESCRIPTION OF THE INVENTION

In one embodiment of the present invention there is provided a process for manufacture of a compound according to formula VII comprising the step contacting a diene of formula II with a penta-coordinated ruthenium (II) carbene complex ring-closing catalyst to afford a compound of formula I wherein $R^1$, $R^2$ and X are as described hereinabove.

In another embodiment of the present invention there is provided a process for the manufacture of a macrocyclic compound according to formula VII comprising the steps of (a) contacting a diene of formula II with a pentacoordinated ruthenium (II) carbene complex ring-closing catalyst to afford a compound of formula I; (b) hydrolyzing the macrocyclic ester of formula I in the presence of a base to form the macrocyclic acid of the formula XX; (c) forming the macrocyclic sulfonamide of formula XXI; (d) treating the macrocyclic sulfonimide of formula XXI with a sodium base to form the salt of the macrocyclic compound of formula VIII wherein $R^1$, $R^2$, $R^3$ and X are as described hereinabove.

SCHEME A

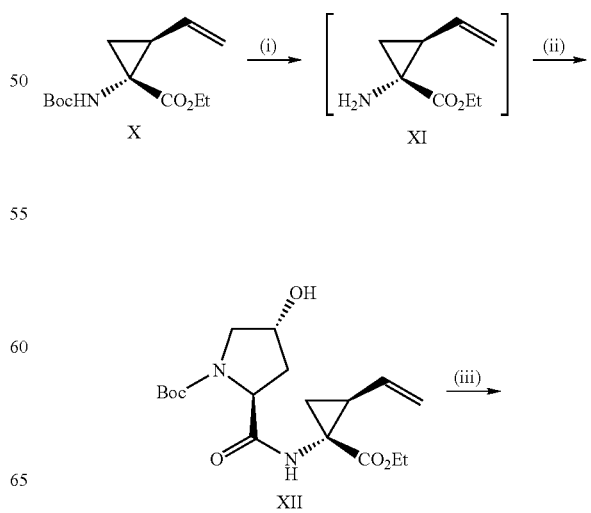

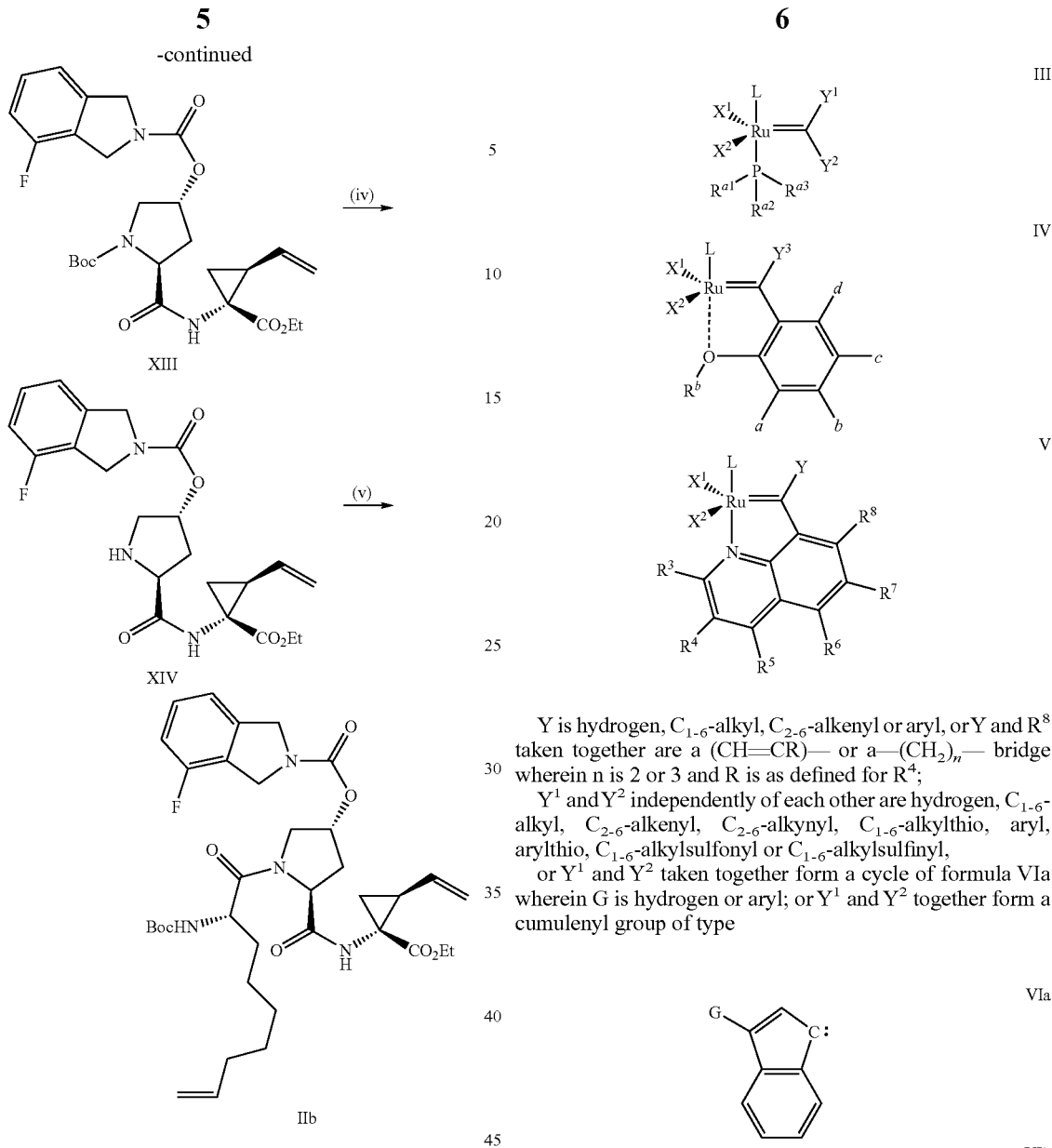

(i)(1). H₂SO₄, EtOAc, 2. (2) 1 eq. TEA; (ii) Boc-(2S,4R)-hydroxyproline (1.0 Eq), 1.05 eq NMM, pivaloyl chloride (1.0 Eq.); (iii) 4-fluoro-2,3-dihydro-1H-isoindole hydrochloride salt; (iv) H₂SO₄, EtOAc, recrystallize from toluene; (v) (S)-2-tert-butoxycarbonylamino-non-8-enoic acid dicyclohexylammonium salt (1.10 Eq.), pivaloyl chloride (1.10 Eq.)

The diene of formula II can be prepared as depicted in SCHEME A. For example the vinylcyclopropancarboxylate X is treated with sulfuric acid to form XI, then coupled with Boc-(2S,4R)-hydroxyproline to form XII. Carbamate formation at the free OH group with 4-fluoroisoindoline leads to XIII and removal of the Boc-protecting group and addition of the (S)-2-tert-butoxycarbonylamino-non-8-enoic acid side chain affords diene IIb.

Step a)

Step a) of the present process is the RCM of II which affords the macrocyclic ester of formula I. The RCM reaction is performed with a pentacoordinated ruthenium (II) carbene complex catalyst selected from compounds of the formula III to IV wherein L is a neutral ligand and $X^1$ and $X^2$ independently of each other are anionic ligands;

Y is hydrogen, $C_{1-6}$-alkyl, $C_{2-6}$-alkenyl or aryl, or Y and $R^8$ taken together are a (CH=CR)— or a—(CH₂)ₙ— bridge wherein n is 2 or 3 and R is as defined for $R^4$;

$Y^1$ and $Y^2$ independently of each other are hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl, or $Y^1$ and $Y^2$ taken together form a cycle of formula VIa wherein G is hydrogen or aryl; or $Y^1$ and $Y^2$ together form a cumulenyl group of type

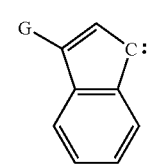

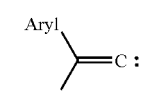

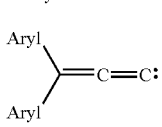

$Y^3$ is hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl;

$R^{a1}$, $R^{a2}$ and $R^{a3}$ independently of each other are $C_{1-6}$-alkyl, $C_{3-7}$-cycloalkyl, aryl or heteroaryl or $R^{a1}$ and $R^{a2}$, or $R^{a2}$ and $R^{a3}$, or $R^{a1}$ and $R^{a3}$ together form a 1,5-bridged cyclooctyl group;

$R^b$ is $C_{1-6}$-alkyl, $C_{2-6}$-alkenyl, halogen-$C_{1-6}$-alkyl, $C_{2-6}$-alkynyl, aryl, $C_{1-6}$-alkoxycarbonyl, $C_{1-6}$-alkylcarbonyl, mono-$C_{1-6}$-alkyl- or di-$C_{1-6}$-alkylamino, $C_{1-6}$-alkylaminocarbonyl, $C_{1-6}$-alkylthiocarbonyl, $C_{1-6}$-alkylsulfonyl, $C_{1-6}$-alkylsulfinyl or arylalkyl;

$R^3$, $R^4$, $R^5$, $R^6$, $R^7$ and $R^8$ are independently hydrogen, $C_{1-6}$-alkyl, halogen-$C_{1-6}$-alkyl, $C_{2-6}$-alkenyl, $C_{2-6}$-alkynyl, halogen-$C_{1-6}$-alkyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, SO$_3$H, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, SO$_3$—$C_{1-6}$-alkyl, OSi($C_{1-6}$-alkyl)$_3$ or SO$_2$—NR'R" wherein R' and R" independently of each other are hydrogen, aryl or $C_{1-6}$-alkyl or R' and R" together with the N atom form a carbocycle;

a, b, c and d independently are hydrogen, $C_{1-6}$-alkyl, halogen-$C_{1-6}$-alkyl, $C_{2-6}$-alkenyl, $C_{2-6}$-alkynyl, halogen-$C_{1-6}$-alkyl, $C_{1-6}$-alkoxy, $C_{2-6}$-alkenyloxy, $C_{2-6}$-alkynyloxy, $C_{1-6}$, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-akylsulfinyl, arylsulfonyl, SO$_3$H, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, SO$_3$—$C_{1-6}$-alkyl, OSi($C_{1-6}$-alkyl)$_3$ or SO$_2$—NR'R" wherein R' and R" independently of each other are hydrogen, aryl or $C_{1-6}$-alkyl or R' and R" together with the N atom form a carbocycle;

The ligand L is a neutral ligand preferably selected from the phosphine, —P($R^{a1}$)($R^{a2}$)($R^{a3}$),

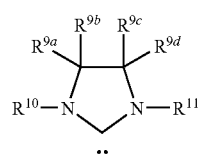

VII

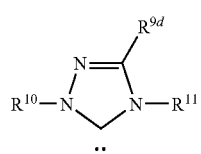

VIII

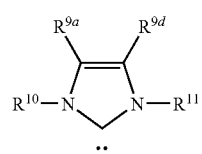

IX or carbene complexes VII, VIII or IX wherein $R^{10}$ and $R^{11}$ independently of each other are $C_{1-6}$-alkyl, aryl, $C_{2-6}$-alkenyl or 1-adamantyl; $R^{9a-d}$ are independently hydrogen, $C_{1-6}$-alkyl, $C_{2-6}$-alkenyl or aryl, or $R^{9b}$ and $R^{9c}$ or $R^{9a}$ and $R^{9d}$ taken together form a-(CH$_2$)$_4$— bridge; $R^{a1-a3}$ are as outlined above, but preferably cyclohexyl or phenyl.

In a preferred embodiment $R^{10}$ and $R^{11}$ are $C_{1-6}$-alkyl or a phenyl group which phenyl is mono-, di- or tri-substituted with $C_{1-6}$-alkyl; more $R^{10}$ and $R^{11}$ preferably have the meaning of t-butyl, 1-adamantyl, isopropyl, 2-methylphenyl, 2,6-diisopropylphenyl or 2,4,6-trimethylphenyl; and, most preferably, 2,4,6-trimethylphenyl.

In a preferred embodiment $R^{9a}$ and $R^{9c}$ are methyl or phenyl and $R^{9b}$ and $R^{9d}$ are hydrogen, or $R^{9a}$ and $R^{9c}$ or $R^{9b}$ and $R^{9d}$ are taken together to form a —(CH$_2$)$_n$— bridge wherein n is 3 or 4. Its hereby understood that if chiral carbon atoms are present, both the racemic and the enantiomerically pure form are comprised.

In a further preferred embodiment $R^{9a-d}$ is hydrogen. In another further preferred embodiment L is wherein $R_{10}$ and $R^{11}$ are as described above.

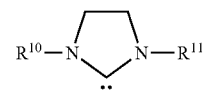

VIIa

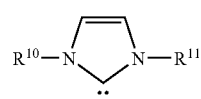

VIIIa

The anionic ligands $X^1$ and $X^2$ are preferably selected from a halogen or a pseudo halogen such as cyanide, a rhodanide, a cyanate, an isocyanate, acetate or trifluoroacetate. Preferred anionic ligands for $X^1$ and $X^2$ are a halogens and chloro is the most preferred anionic ligand.

Y preferably is hydrogen; $Y^1$ and $Y^2$ are the same or different and preferably are hydrogen, $C_{1-6}$-alkyl, $C_{2-6}$-alkenyl, $C_{1-6}$-alkylthio, phenyl or phenylthio, or $Y^1$ and $Y^2$ taken together form a cycle of the type VI wherein G is hydrogen or phenyl; $Y^3$ preferably is hydrogen. $R^b$ is as outlined above, but preferably is $C_{1-6}$-alkyl or halogen-$C_{1-6}$-alkyl. The preferred meaning for a, b and d is hydrogen.

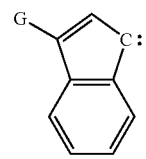

VI

The preferred meaning for c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino or SO$_2$—NR'R" wherein R' and R" independently of each other are hydrogen, $C_{1-6}$-alkyl, aryl or R' and R" together with the N atom form a carbocycle; The more preferred meaning for c is hydrogen, Cl, nitro or SO$_2$—NR'R".

In one embodiment of the present invention there is provided a process for manufacture of a compound according to formula VII comprising the step contacting a diene of formula II with a penta-coordinated ruthenium (II) carbene complex ring-closing catalyst to afford a compound of formula I wherein $R^1$, $R^2$ and X are as described hereinabove.

The following catalysts represent preferred pentacoordinated ruthenium (II) carbene complex catalysts

| Catalyst structure | Chemical Name |
| --- | --- |
| (structure) | [RuCl$_2$(PCy$_3$)$_2$(benzylidene)] |
| (structure) | [RuCl$_2$(PCy$_3$)(ImH$_2$Mes)(benzylidene)] |
| (structure) | [RuCl$_2$(=CH(2-iPrOPh))(PCy$_3$)] |
| (structure) | [RuCl$_2$(=CH(2-iPrOPh))(ImH$_2$Mes)] |
| (structure) | [RuCl$_2$(=CH—CH=CMe$_2$)(P(Cyp)$_3$)$_2$] |
| (structure) | [RuCl$_2$(PCy$_3$)$_2$(3-phenylindenyl-1-idene)] |
| (structure) | [RuCl$_2$(=CHPh)(ImH$_2$Pr)(PCy$_3$)] |
| (structure) | [RuCl$_2$(PCy$_3$)(ImH$_2$Mes)(3-phenyl-indenyl-1-idene)] |

-continued

| Catalyst structure | Chemical Name |
|---|---|
| | [RuCl$_2$(=CH(2-iPrO, 5-NO$_2$Ph))(ImH$_2$Mes)] |
| | [RuCl$_2$(3-phenylindenyl-1-idene)(ImMes)-(PCy$_3$)] |
| | [RuCl$_2$(3-phenylindenyl-1-idene)(ImMes)-(PPh$_3$)] |
| | [RuCl$_2$(=CH(2-iPrO, 5-ClPh))(ImH$_2$Mes)] |
| | [RuCl$_2$(=CH(7-CF$_3$, 5-Cl-8-quinoline))-(ImH$_2$Mes)] |
| | [RuCl$_2$(=CH(2-iPrO, 5-SO$_2$NMe$_2$Ph))-(ImH$_2$Mes)] |

-continued

| Catalyst structure | Chemical Name |
| --- | --- |
| | [RuCl$_2$(=CHPh)(ImMes)(PCy$_3$)] |
| | [RuCl$_2$(=CHSPh)(ImH$_2$Mes)(PCy$_3$)] |
| | [RuCl$_2$(3-phenylindenyl-1-idene)-(isobutylphobane)$_2$] |
| | [RuCl$_2$(=CH(2-iPr, 5-SO$_2$NMe$_2$Ph))(PCy$_3$)] |
| | [RuCl$_2$(=CHPh)(ImH$_2$oTol)(PCy$_3$)] |
| | [RuCl$_2$(=CHCH=CMe$_2$)(PCy$_3$)$_2$] |

| Catalyst structure | Chemical Name |
|---|---|
|  | [RuCl₂(=CH(2-iPrOPh))(ImH₂oTol)] |
|  | [RuCl₂(=CH—CH=CMe₂)(ImH₂Mes)(PCy₃)] |

More preferred catalysts are: [RuCl₂(PCy₃)(ImH₂Mes) (benzylidene)], [RuCl₂(PCy₃)(ImH₂Mes)(3-phenylindenyl-1-idene)], [RuCl₂(3-phenylindenyl-1idene)(ImMes)(PCy₃)] and [RuCl₂(=CH(2-iPrO, 5-SO₂NMe₂Ph))(ImH₂Mes)].

The RCM reaction is usually performed in an organic solvent, preferably in an aromatic organic solvent such as in benzene, toluene or mesitylene or in halogenated aromatic solvents such as in polyfluorinated benzenes or toluenes. Also halogenated hydrocarbons such as dichloromethane or dichloroethane are suitable solvents. The solvents may be used as single solvent or as a mixture of different solvents. In addition a co-solvent selected from an aliphatic hydrocarbon such as pentane, hexane or heptane may be used as well. It is convenient to run the reaction either by bubbling an inert gas through the reaction mixture or under a slight vacuum.

In one embodiment of the present invention the ring closure is carried out at one of the aforementioned catalysts at a reaction temperature selected in a range of 20° C. to 140° C., preferably 40 to 100° C. and even more preferred 50° C. to 90° C. In another embodiment the molar substrate to catalyst ratio S/C is usually selected in a range of 20 to 10000, but preferably in a range of 200 to 4000.

The macrocyclic ester of formula I can be isolated by applying methods known to the skilled in the art such as by column chromatography or by crystallisation. The metathesis reaction mixture can also, after a simple extractive work-up, be used directly into the next step.

In order to remove most catalyst from the solution of the macrocyclic ester I it is convenient to treat the reaction mixture with a complexing agent such as ethylenediamine and to extract the resulting soluble ruthenium species into aqueous acid. The amount of ethylenediamine is not critical; it can be used in a 1:1 to 100:1 molar ratio relative to the catalyst, preferentially in 20:1 to 70:1 molar ratio.

Step b)

Step b entails the hydrolysis of the macrocyclic ester of formula I affording the macrocyclic acid of formula XX. In a preferred embodiment the macrocyclic ester of the formula I wherein $R^1$ is Boc, $R^2$ is ethyl and X represents a 4-fluoro substituent.

The hydrolysis can usually be accomplished by treatment with an aqueous alkali hydroxide solution such as with an aqueous sodium hydroxide solution in solvents like methanol or ethanol at a temperature of 0° C. to 40° C.

After neutralization of the reaction mixture, usually with hydrochloric acid, the macrocyclic acid of formula XX can be isolated by extraction into a suitable solvent such as with dichloromethane. Crystallization from a suitable solvent, preferably in tetrahydrofuran leads to a crystalline product with a purity of over 98%.

Step c)

Step c requires the coupling of the macrocyclic acid of formula XX with cyclopropyl sulfonamide to form the macrocyclic sulfonamide of formula XXI. In a preferred embodiment the macrocyclic acid is a compound of formula XX wherein $R^1$ is Boc and X represents a 4-fluoro substituent is used.

In a first step the macrocyclic acid of formula XX is reacted with acetic acid anhydride in the presence of an inorganic base, such as with an alkali carbonate like sodium carbonate and a suitable organic solvent such as with tetrahydrofuran which produces an azlactone intermediate of the formula XXIII wherein $R^1$ is an amino protecting group and X is halogen.

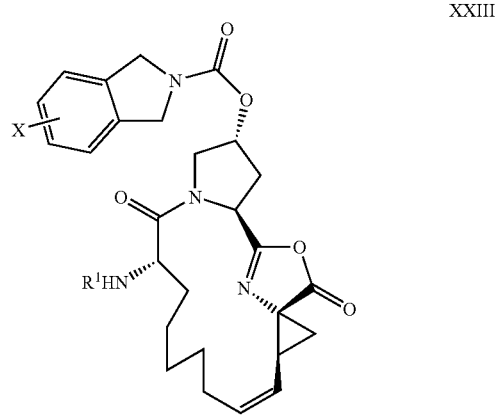

XXIII

The reaction is expediently performed at a temperature of 10° C. to 50° C. As a rule the azlactone intermediate will not be isolated but reacted in situ with cyclopropyl sulfonamide in the presence of an inorganic base, such as with an alkali carbonate like potassium carbonate to afford the macrocyclic sulfonamide of formula XXI. The reaction in this second step is expediently performed at a temperature of 50° C. to 70° C.

Upon completion of the reaction the reaction mixture can be treated with water. After separation and removal of the water phase the organic phase may further be diluted with a suitable organic solvent such as with ethyl acetate or toluene and washed e.g. with an aqueous sulphuric acid and water.

Isolation of the macrocyclic sulfonamide of formula XXI can then be accomplished by a solvent switch to ethanol followed by addition of the ethanolic solution to water thereby causing precipitation of the desired product. However, in a preferred embodiment the macrocyclic sulfonamide of formula XXI will not be isolated, but the organic phase which has been treated as hereinbefore described will be freed of residual water by a continuous azeotropic distillation which results in a mixture can then directly be used for subsequent step d.

Step d)

Step d requires the treatment of the macrocyclic sulfonamide of formula XXI with a sodium base to form the end product, i.e. the macrocyclic compound of formula VII. In a preferred embodiment the macrocyclic sulfonamide of the formula XXI wherein $R^1$ is Boc and X represents a 4-fluoro substituent is used.

As a rule the water free mixture obtained from step c) is treated with a sodium base sodium hydroxide, preferably an aqueous solution thereof, sodium methylate or sodium ethoxide, preferably with sodium methylate in the presence of methanol at a temperature of 0° C. and 50° C. Upon completion of the reaction the reaction mixture can be treated with a mixture of a suitable organic solvent such as ethyl acetate and water where after the crystals of the sodium salt of formula VII, preferably the compound of formula VIII can be collected in good purity and yield.

The following definitions are set forth to illustrate and define the meaning and scope of the various terms used to describe the invention herein.

The term "amino protecting group" refers to any substituents conventionally used to hinder the reactivity of the amino group. Suitable amino protecting groups are described in Green T., "Protective Groups in Organic Synthesis", Chapter 7, John Wiley and Sons, Inc., 1991, 309-385. Suitable amino protecting groups are Fmoc, Cbz, Moz, Boc, Troc, Teoc or Voc. Preferred amino protecting group, as defined for $R^1$ is Boc.

The term "halogen" refers to fluorine, chlorine, bromine and iodine. The preferred halogen as a rule is chlorine, while the preferred halogen for X is fluorine.

In a preferred embodiment the moiety of the formula

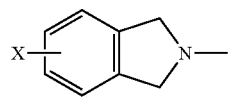

stands for

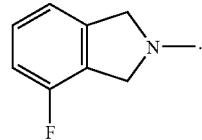

The term "$C_{1-6}$-alkyl", alone or in combination with other groups, refers to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl and pentyl or hexyl and its isomers.

The term "$C_{1-4}$-alkyl" as used in herein for $R^2$ refers to a branched or straight-chain monovalent saturated aliphatic hydrocarbon radical of one to four carbon atoms such as methyl, ethyl, n-propyl, isopropyl, n-butyl, s-butyl, t-butyl, preferably to ethyl.

The term "$C_{2-6}$-alkenyl", alone or in combination with other groups, refers to a branched or straight-chain monovalent unsaturated aliphatic hydrocarbon radical of two to six carbon atoms, preferably two to four carbon atoms. This term is further exemplified by radicals as vinyl, propenyl, butenyl, pentenyl and hexenyl and their isomers. Preferred alkenyl radical is vinyl.

The term "$C_{2-6}$-alkynyl", alone or in combination with other groups, refers to a branched or straight-chain monovalent unsaturated aliphatic hydrocarbon radical of two to six carbon atoms, preferably two to four carbon atoms. This term is further exemplified by radicals as ethynyl, propynyl, butynyl, pentynyl or hexynyl their isomers.

The term "halogen-$C_{1-6}$-alkyl" refers to a halogen substituted $C_{1-6}$-alkyl radical wherein halogen has the meaning as above. Preferred "halogen-$C_{1-6}$-alkyl" radicals are the fluorinated $C_{1-6}$-alkyl radicals such as $CF_3$, $CH_2CF_3$, $CH(CF_3)_2$, $CH(CH_3)(CF_3)$, $C_4F_9$.

The term "$C_{1-6}$-alkoxy" refers to a branched or straight-chain monovalent saturated aliphatic hydrocarbon radical of one to six carbon atoms, preferably 1 to 4 carbon atoms attached to an oxygen atom. Examples of "alkoxy" are methoxy, ethoxy, propoxy, isopropoxy, butoxy, isobutoxy and hexyloxy. Preferred are the alkoxy groups specifically exemplified herein.

The alkyl chain of the alkoxy group can optionally be substituted, particularly mono-, di- or tri-substituted by alkoxy groups as defined above, preferably methoxy, or ethoxy or by aryl groups, preferably henyl. Preferred substituted alkoxy group is the benzyloxy group.

The term "$C_{1-6}$-alkyl carbonyl" refers to $C_{1-6}$-alkyl substituted carbonyl group, preferably to a $C_{1-4}$-alkycarbonyl group. It includes for example acetyl, propanoyl, butanoyl or pivaloyl. Preferred alkyl carbonyl group is acetyl.

The term "$C_{1-6}$-alkylthio" refers to the group $C_{1-6}$-alkyl-S—, preferably $C_{1-4}$-alkyl e.g. methylthio or ethylthio. Preferred are the alkylthio groups specifically exemplified herein.

The term "arylthio" refers to a group aryl-S—, preferably to phenylthio.

The term "$C_{1-6}$-alkylsulfonyl" refers to a $C_{1-6}$-alkyl substituted sulfonyl group, preferably to methylsulfonyl.

The term "$C_{1-6}$-alkylsulfinyl" refers to a $C_{1-6}$-alkyl substituted sulfinyl group, preferably to methylsulfinyl.

The term "$SO_2$-aryl" refers to a sulfonyl substituted aryl radical. Preferred $SO_2$-aryl radical is $SO_2$-phenyl.

The term "SO$_2$—NR'R''" refers to a sulfonyl group substituted with an amino group NR'R'' wherein R' and R'' independently of each other have the meaning of hydrogen or C$_{1-6}$-alkyl or R' and R'' together with the N atom form a carbocycle, e.g. —(CH$_2$)$_4$— or —(CH)$_4$—. Preferred SO$_2$—NR'R'' radical is SO$_2$—N(CH$_3$)$_2$.

The term "mono- or di-C$_{1-6}$-alkyl-amino" refers to an amino group, which is mono- or disubstituted with C$_{1-6}$-alkyl, preferably C$_{1-4}$-alkyl. A mono-C$_{1-6}$-alkyl-amino group includes for example methylamino or ethylamino. The term "di-C$_{1-6}$-alkyl-amino" includes for example dimethylamino, diethylamino or ethylmethylamino. Preferred are the mono- or di-C$_{1-4}$-alkylamino groups specifically exemplified herein. It is hereby understood that the term "di-C$_{1-6}$-alkyl-amino" includes ring systems wherein the two alkyl groups together with the nitrogen atom to which they are attached form a 4 to 7 membered heterocycle which also may carry one further hetero atom selected from nitrogen, oxygen or sulfur.

The term "cycloalkyl" denotes a "C$_{3-7}$-cycloalkyl" group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono-, di-, tri- or multiply-substituted by halogen, hydroxy, CN, halogen-C$_{1-6}$-alkyl, NO$_2$, NH$_2$, NH(alkyl), N(alkyl)$_2$, carboxy, aminocarbonyl, alkyl, alkoxy, alkylcarbonyl, C$_{1-6}$-alkylsulfonyl, SO$_2$-aryl, SO$_3$H, SO$_3$-alkyl, SO$_2$—NR'R'', aryl and/or aryloxy. Preferred aryl group is phenyl.

The term "aryloxy" relates to an aryl radical attached to an oxygen atom. The term "aryl" has the meaning as defined above. Preferred aryloxy group is phenyloxy.

The term "arylalkyl" relates to an aryl radical attached to an alkyl group. The term "aryl" has the meaning as defined above. Preferred arylalkyl group is benzyl.

The term "heteroaryl" relates to a heterocyclic aryl radical containing 1 to 3 heteroatoms in the ring with the remainder being carbon atoms. Suitable heteroatoms include, without limitation, oxygen, sulfur, and nitrogen. Exemplary heteroaryl groups include furanyl, thienyl, pyridyl, pyrrolyl, N-alkyl pyrrolo, pyrimidyl, pyrazinyl, imidazolyl, benzofuranyl, quinolinyl, and indolyl. Like the aryl group the heteroaryl group can optionally be mono-, di-, tri- or multiply-substituted by halogen, hydroxy, CN, NO$_2$, NH$_2$, NH(alkyl), N(alkyl)$_2$, carboxy, aminocarbonyl, alkyl, alkoxy, alkylcarbonyl, C$_{1-6}$-alkylsulfonyl, SO$_2$-aryl, SO$_3$H, SO$_3$-alkyl, SO$_2$—NR'R'', aryl and/or aryloxy.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R'' appears twice and is defined as "independently carbon or nitrogen", both R''s can be carbon, both R''s can be nitrogen, or one R'' can be carbon and the other nitrogen.

When any variable (e.g., R$^1$, R$^{4a}$, Ar, X$^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

EXAMPLES

Abbreviations r.t.=room temperature
Boc=tert-butoxycarbonyl
ImH$_2$Mes=1,3-bis-(2,4,6-trimethylphenyl)-2-imidazolidinylidene
ImMes=1,3-bis-(2,4,6-trimethylphenyl)-2-imidazolylidene
ImH$_2$Pr=1,3-bis-(2,6-diisopropylphenyl)-2-imidazolidinylidene RCM=ring closing metathesis RP column=reverse phase column S/C=molar substrate-to-catalyst ratio Mes=2,4,6-trimethylphenyl Cy=cyclohexyl Cyp=cyclopentyl Diene IIb=4-Fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester of the formula

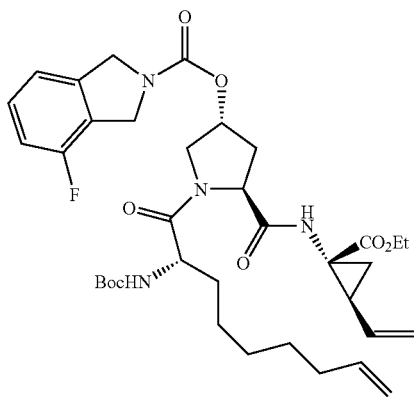

IIb

RCM-Ester Ib=(2R,6S,12Z,13aS,14aR,16aS)-Cyclopropa[e]pyrrolo[1,2-a][1,4]diazacyclopentadecine-14a(5H)-carboxylic acid, 6-[[(tert-butoxy)carbonyl]amino-2-[[(4-fluoro-1,3-dihydro-2H-isoindol-2-yl)carbonyl]oxy]-1,2,3,6,7,8,9,10,11,13a,14,15,16,16a-hexadecahydro-5,16-dioxo-, ethyl ester The atom numbering is as shown below:

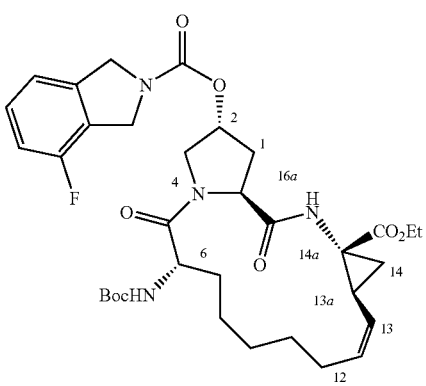

Ib

Epi-Ib=13aR epimer of RCM ester of formula Ib

Epi-IIb: epimer at the vinyl substituted carbon atom of cyclopropyl unit in IIb a %=HPLC area %

Example A

Preparation of the diene of formula IIb i.e. 4-fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester a) (1R,2S)-1-Amino-2-vinyl-cyclopropanecarboxylic acid ethyl ester A suspension of 5.11 g (20.0 mmol) of (1R,2S)-1-tert-butoxycarbonylamino-2-vinyl-cyclopropanecarboxylic acid ethyl ester (commercially available from Synthetech Oregon, USA) in 1.94 mL of ethyl acetate was cooled to 8° C. using an ice bath. Then a solution of 2.17 g (21.0 mmol) of sulfuric acid in 4.0 mL of ethyl acetate was added in 5 min. The ice bath was removed and the reaction mixture was stirred for 30 min at room temperature and 1 h at 50° C. The reaction mixture was then cooled to room temperature and used in the next step without further purification.

b) (2S,4R)-2-((1R,2S)-1-Ethoxycarbonyl-2-vinyl-cyclopropylcarbamoyl)-4-hydroxy-pyrrolidine-1-carboxylic acid tert-butyl ester To a solution of 4.87 g (21.0 mmol) of Boc-(2S,4R)-hydroxyproline in 25 mL of THF was added 2.03 mL (20.0 mmol) of N-methylmorpholine. A suspension formed. The mixture was cooled to −23° C. and 2.85 g (20.0 mmol) of isobutylchloroformate was added. After stirring for 10 min additional 4.25 g (42.0 mmol) of N-methylmorpholine was added. To this mixture was added the solution of (1R,2S)-1-amino-2-vinyl-cyclopropanecarboxylic acid ethyl ester prepared in example 1 at a temperature of −15° C. within 5 min. The reaction mixture was stirred for 2.5 h at 0° C. The salts were filtered off and the filtrate was treated with 20 mL of aqueous HCl (0.5 N). The solvents were removed at 50° C. under reduced pressure using a rotary evaporator and the residue was extracted twice with 50 mL of ethyl acetate. The extract was washed with 40 mL of water and 40 mL of aqueous sodium carbonate solution (10% w/w), and dried over sodium sulfate. Finally the solvent was removed completely to give 8.19 g of (2S,4R)-2-((1R,2S)-1-ethoxycarbonyl-2-vinyl-cyclopropylcarbamoyl)-4-hydroxy-pyrrolidine-1-carboxylic acid tert-butyl ester as a yellow oil. The product was used in the next step without further purification.

c) 4-Fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester 8.19 g of crude (2S,4R)-2-((1R,2S)-1-ethoxycarbonyl-2-vinyl-cyclopropylcarbamoyl)-4-hydroxy-pyrrolidine-1-carboxylic acid tert-butyl ester was dissolved in 60 mL of toluene and 4.25 g carbonyldiimidazole (26.2 mmol) was added in portions at a temperature of 22° C. to 25° C. The reaction mixture was stirred for 1.5 h at ambient temperature. Then 3.66 g (21.0 mmol) of 4-fluoroisoindoline hydrochloride was added in portions followed by 3.1 mL of triethylamine. The resulting suspension was heated to 52° C. bath temperature. After stirring for 3 h at this temperature the reaction mixture was cooled with an ice bath and 70 mL of aqueous HCl (1M) were added. The mixture was extracted with 50 mL of toluene. The separated aqueous layer was extracted twice with 50 mL toluene. The combined toluene extracts were washed with 30 mL of water and 30 mL of an aqueous solution of sodium carbonate (5% w/w). The toluene extract was dried with sodium sulfate, filtered, and the solvent was completely removed to afford 9.21 g of 4-fluoro-1,3-dihydro-isoindole-2-carboxylic acid (3R,5S)-1-tert-butoxycarbonyl-5-((1R,2S)-1-ethoxycarbonyl-2-vinyl-cyclopropylcarbamoyl)-pyrrolidin-3-yl ester as a grey solid, which was used in the next step without further purification.

MS: 532.3 (M$^+$+H). $^1$H-NMR (400 MHz, DMSO-D6, 79.2° C.): 8.40 (s, 1H), 7.37-7.31 (m, 1H), 7.16 (d, J=7.5 Hz, 1H), 7.09-7.05 (m, 1H), 5.73-5.64 (m, 5H), 5.24 (dd, J=17.2, 1.6 Hz, 1H), 5.18 (m, 1H), 5.08 (dd, J=10.4, 1.6 Hz, 1H), 4.67 (m, 4H), 4.22 (t, J=7.7 Hz, 1H), 4.11-4.00 (m, 2H), 3.66 (dd, J=11.9, 4.7 Hz, 1H), 3.54 (d, br, 12.1 Hz, 1H), 2.37-2.28 (m, 1H), 2.19-2.11 (m, 2H), 1.63 (dd, J=7.95, 5.25 Hz, 1H), 1.38 (s, 9H), 1.28 (dd, J=9.4, 5.1 Hz, 1H), 1.16 (t, J=7.0 Hz, 3H).

d) 4-Fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester A solution of 2.15 g (21.0 mmol) of sulfuric acid in 3.9 mL of ethyl acetate was added to a suspension of 9.21 g of crude 4-fluoro-1,3-dihydro-isoindole-2-carboxylic acid (3R,5S)-1-tert-butoxycarbonyl-5-((1R,2S)-1-ethoxycarbonyl-2-vinyl-cyclopropyl-carbamoyl)-pyrrolidin-3-yl ester in 31 mL of ethyl acetate, which was cooled with an ice bath. The ice bath was removed and the reaction mixture was heated to 50° C. for 3 h until all starting material had been consumed. To the reaction mixture an aqueous solution of sodium carbonate (10% w/w) was added. Phases were separated and the aqueous layer was extracted three times with ethyl acetate. The combined organic extracts were evaporated to dryness and the residue was dissolved in 85 mL of toluene and heated to 102° C. The solution was slowly cooled to 2° C. Crystallization started at 53° C. The crystals were filtered off and dried under reduced pressure to yield 6.62 g (77% over four steps starting from 20.0 mmol (1R,2S)-1-tert-butoxycarbonylamino-2-vinyl-cyclopropanecarboxylic acid ethyl ester; yield not corrected for assay; assay: 97.9% area HPLC) of 4-fluoro-1,3-dihydro-isoindole-2-carboxylic acid (3R,5S)-5-((1R,2S)-1-ethoxycarbonyl-2-vinyl-cyclopropyl-carbamoyl)-pyrrolidin-3-yl ester as grey crystals.

MS: 432.2 (M$^+$+H). $^1$H-NMR (400 MHz, CDCl$_3$): 8.17 (d, J=4.0 Hz, 1H), 7.31-7.25 (m, 1H), 7.08-6.95 (m, 2H), 5.82-5.73 (m, 1H), 5.31 (dd, J=16.4, 1.2 Hz, 1H), 5.29 (m, 1H), 5.13 (dd, J=10.3, 1.7 Hz), 4.82-4.65 (m, 2H), 4.23-4.07 (m, 2H), 3.98 (m, 1H), 3.28 (d, 13.0 Hz, 1H), 3.07-3.02 (m, 1H), 2.46-2.40 (m, 1H), 2.30 (s, br, 1H), 2.26-2.17 (m, 1H), 2.12 (m, 1H), 1.92 (dd, J=7.9, 5.5 Hz, 1H), 1.6-1.56 (m, 1H), 1.24 (t, J=7.1 Hz, 3H).

e) 4-Fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester A solution of 1.15 g (2.55 mmoL) (S)-2-tert-butoxycarbonylamino-non-8-enoic acid dicyclohexylammonium salt (commercially available from Synthetech Oregon, USA) and 469 mg (4.64 mmol) N-methylmorpholine in 9.0 mL of THF was added dropwise to a solution of 302 mg (2.53 mmol) pivaloyl chloride in 1.5 mL of THF while maintaining the temperature at 20-25° C. The suspension was stirred for 45 min, then cooled to 0° C. A solution of 1.00 g (2.32 mmol) of 4-Fluoro-1,3-dihydro-isoindole-2-carboxylic acid (3R,5S)-5-((1R,2S)-1-ethoxycarbonyl-2-vinyl-cyclopropylcarbamoyl)-pyrrolidin-3-yl ester in 13 mL of THF was added to the mixed anhydride at 0° C. within 25 min. The mixture was first stirred for 2.5 h at 2° C., then for 19 h at 26° C. 9.5 mL water and 14.8 mL aqueous HCl (0.5 N) were added. The phases were separated and the aqueous layer was extracted with toluene (3×3 mL). The combined organic layers were washed with 2 mL of water, 5 mL of aqueous sodium carbonate (5% w/w) and dried over sodium sulfate. The solvent was removed at 50° C. under reduced pressure using a rotary evaporator. The resulting oil was finally dried under oil pump vacuum yielding 1.75 g (88.3%) of 4-fluoro-1,3-dihydro-isoindole-2-carboxylic acid (3R,5S)-1-((S)-2-tert-butoxycarbonylamino-non-8-enoyl)-5-((1R,2S)-1-ethoxycarbonyl-2-vinyl-cyclopropylcarbamoyl)-pyrrolidin-3-yl ester as a brown resin with an assay of 80.5% m/m.

RCM Examples

Table of Catalysts tested:

| Catalyst Number | Catalyst Structure | Chemical Name |
|---|---|---|
| 5000 | | [RuCl$_2$(PCy$_3$)$_2$(benzylidene)] CAS No. 172222-30-9; a) |
| 5001 | | [RuCl$_2$(PCy$_3$)(ImH$_2$Mes)(benzylidene)] CAS No. 246047-72-3; a) |

-continued

Table of Catalysts tested:

| Catalyst Number | Catalyst Structure | Chemical Name |
| --- | --- | --- |
| 5002 | | [RuCl$_2$(=CH(2-iPrOPh))(PCy$_3$)]<br>CAS No. 203714-71-0; a) |
| 5003 | | [RuCl$_2$(=CH(2-iPrOPh))(ImH$_2$Mes)]<br>CAS No. 301224-40-8; a) |
| 5004 | | [RuCl$_2$(=CH—CH=CMe$_2$)(P(Cyp)$_3$)$_2$]<br>CAS No. 220883-08-9; a) |
| 5006 | | [RuCl$_2$(PCy$_3$)$_2$(3-phenylindenyl-1-idene)]<br>CAS No. 250220-36-1; c) |
| 5007 | | [RuCl$_2$(=CHPh)(ImH$_2$Pr)(PCy$_3$)]<br>CAS No. 373640-75-6;<br>Prepared according to: M. D. Dinger, J. C. Mol, Adv. Synth. Catal. 2002, 344, 671. |
| 5008 | | [RuCl$_2$(PCy$_3$)(ImH$_2$Mes)(3-phenylindenyl-1-idene)]<br>CAS No. 536724-67-1; c) |
| 5014 | | [RuCl$_2$(=CH(2-iPrO, 5-NO$_2$Ph))(ImH$_2$Mes)]<br>CAS No. 502964-52-5;<br>Prepared according to K. Grela, S. Harutyunyan, A. Michrowska, Angew. Chem. Int. Ed. 2002, 41, 4038. |

-continued

Table of Catalysts tested:

| Catalyst Number | Catalyst Structure | Chemical Name |
|---|---|---|
| 5016 | | [RuCl$_2$(3-phenylindenyl-1-indene)(ImMes)(PCy$_3$)] CAS No. 254972-49-1; d) |
| 5017 | | [RuCl$_2$(3-phenylindenyl-1-idene)(ImMes)(PPh$_3$)] CAS No. 254972-47-9; d) |
| 5024 | | [RuCl$_2$(=CH(2-iPrO, 5-ClPh))(ImH$_2$Mes)] CAS No. 918870-68-5; b) |
| 5025 | | [RuCl$_2$(=CH(7-CF$_3$, 5-Cl-8-quinoline))(ImH$_2$Mes)]; e) |
| 5028 | | [RuCl$_2$(=CH(2-iPrO, 5-SO$_2$NMe$_2$Ph)(ImH$_2$Mes))] CAS No. 918870-76-5; b) |
| 5033 | | [RuCl$_2$(=CHPh)(ImMes)(PCy$_3$)] CAS No. 223415-64-3; Prepared accordino to S. P. Nolan et al, Organometallics 2002, 21, 442. |

| Catalyst Number | Catalyst Structure | Chemical Name |
| --- | --- | --- |
| 5040 | | [RuCl$_2$(=CHSPh)(ImH$_2$Mes)(PCy$_3$)]; g) |
| 5041 | | [RuCl$_2$(3-phenylindenyl-1-idene)-(isobutylphobane)$_2$]<br>CAS No. 894423-99-5; c) |
| 5042 | | [RuCl$_2$(=CH(2-iPrO, 5-SO$_2$NMe$_2$Ph))(PCy$_3$)]<br>CAS No. 918871-44-0; b) |
| 5043 | | [RuCl$_2$(=CHPh)(ImH$_2$oTol)(PCy$_3$)]<br>CAS No. 927429-60-5; a) |

-continued

Table of Catalysts tested:

| Catalyst Number | Catalyst Structure | Chemical Name |
|---|---|---|
| 5045 | | [RuCl$_2$(=CHCH=CMe$_2$)(PCy$_3$)$_2$]<br>CAS No. 194659-03-5; a) |
| 5046 | | [RuCl$_2$(=CH(2-iPrOPh))(ImH$_2$oTol)]<br>CAS No. 927429-61-6; a) |
| 5048 | | [RuCl$_2$(=CH—CH=CMe$_2$)(ImH$_2$Mes)(PCy$_3$)]<br>CAS No. 253688-91-4; a) | a) Commercially available from Sigma-Aldrich Chemie GmbH, Postfach, CH-9471 Buchs, Switzerland:
b) Commercially available from Zannan Pharma Ltd. 4299 Jindu Road, Bid. 3, Shanghai, 201108, P.R. China and Strem Chemicals Inc., 7 Mulliken Way, Newburyport, Mass. 01950-4098, USA.
c) Commercially available from Umicore & Co., Rodenbacher Chaussee 4, D-63403 Hanau, Germany and Strem Chemicals Inc., 7 Mulliken Way, Newburyport, Mass. 0 1950-4098, USA.
d) Commercially available from Degussa AG, Rodenbacher Chaussee 4, D-63403 Hanau, Germany.
e) [RuCl$_2$(ImH$_2$Mes)((4-chloro-2-trifluoromethyl-8-quinolinyl)methylene)]
A suspension of 1.39 g (1.64 mmol) of [RuCl$_2$(PCy$_3$)(ImH$_2$Mes)(phenylmethylene)], 0.17 g (1.80 mmol) copper chloride and 464 mg (1.69 mmol) 4-chloro-2-trifluoromethyl-8-vinyl-quinoline in 100 mL methylene chloride was stirred at 30° C. for 90 min. The reaction mixture was evaporated to dryness and the isolated crude product purified by silica gel chromatography (hexane/ethyl acetate 5:2) to yield 278 mg (24%) of the title compound as green crystals. MS: 721.2 (M$^+$). $^1$H-NMR (300 MHz, CD$_2$Cl$_2$): 2.85 (s, 6H); 2.40 (s, 12H); 4.05 (s, 4H); 7.01 (s, 4H); 7.54 (s, 1H); 7.56 (t, J=7.7 Hz, 1H); 7.65 (d, J=6.8 Hz, 1H); 8.51 (d, J=8.4 Hz, 1H); 16.70-17.10 (br, 1H).
f) Commercially available from Johnson Matthey PCT, 28 Cambridge Science Park, Milton Road, Cambridge, CB4 0FP, UK.
g) Commercially available from Strem Chemicals, Inc., Postfach 1215, KEHL, 77672, Germany.

Example 1

In a glove-box (O$_2$<2 ppm) a solution of 50.0 mg (0.073 mmol, corrected by content) of diene IIb and 2.37 mg (0.036 mmol) of catalyst 5024 in 6.5 mL of toluene (distilled under argon) was stirred at 65° C. in a 15 mL screw-capped flask. After 4 h one drop of ethylene diamine was added and the mixture was stirred for 10 min outside of the glove box. After addition of 1 mL of 1 M aqueous solution of hydrochloric acid the biphasic mixture was stirred for 10 min. A 0.5 mL aliquote of the organic phase was removed and evaporated to dryness; the oily residue was dissolved in 1 mL of acetonitrile and analyzed by HPLC. Conversion was 97 area % and the desired product (RCM-ester Ib) had 72 area % purity.

HPLC method on reverse phase (RP) column: Waters XBridge C18 column, 4.6×150 mm, solvent A: water/acetonitrile 95/5, solvent B: acetonitrile, gradient from A/B 50/50 to 10/90 within 11 min, then 4 min at 10/90, 40° C., 210 nm, 1 mL/min. Retention times: toluene 5.2 min, diene I 8.85 min, RCM-ester Ib 6.97 min (identified by HPLC/MS, [MH]$^+$ 657.4 u), peaks of dimeric by-products at 10.2, 10.4, 12.1 and 13.1 min (MS: [MH]$^+$1313 u). Only the sum of the dimer peaks is given in the tables and experiments.

HPLC method on chiral column: Chiralcel OD-RH, 4.6-150 mm, solvent A: water +5% acetonitrile (62%), acetonitrile (38%), no gradient, 40° C., 1 mL/min, 210 nm. Retention times: diene IIb 83.4 min, 2R epimeric diene epi-IIb 74.2 min, RCM ester I-b 47.6 min, at 13a epimeric RCM-ester Ib (Epi-Ib) 33.9 min.

Examples 2a-2z

The examples in Table 1 were carried out using the same procedure and conditions as in Example 1, but in the presence of various catalysts.

TABLE 1

| Reaction Nr. | Catalyst Nr. | RP column | | | Chiral column | |
|---|---|---|---|---|---|---|
| | | Diene IIb (area %) | RCM-ester Ib (area %) | Dimers (area %) | RCM ester Ib (area %) | Ib/epi-Ib |
| 2a | 5000 | 12 | 52 | 4 | 42 | 65/35 |
| 2b | 5001 | 2 | 69 | 11 | 93 | 97/3 |
| 2c | 5002 | 6 | 66 | 4 | 65 | 87/13 |
| 2d | 5003 | 0.8 | 71 | 13 | 94 | 99/1 |
| 2e | 5004 | 60 | 20 | 2 | 8 | 33/67 |
| 2f | 5005 | 63 | 14 | 1 | 14 | 94/6 |
| 2g | 5006 | 11 | 54 | 4 | 41 | 64/33 |
| 2h | 5007 | 1.5 | 77 | 12 | 86 | 89/11 |
| 2i | 5008 | 4 | 67 | 11 | 92 | 97/3 |
| 2j | 5014 | 2 | 69 | 11 | 95 | 98/2 |
| 2k | 5016 | 3 | 67 | 11 | 91 | 96/4 |
| 2l | 5017 | 3 | 66 | 9 | 87 | 93/7 |
| 2m | 5025 | 75 | 17 | 0.4 | 17 | >99/1 |
| 2n | 5028 | 0.6 | 75 | 14 | 92 | 94/6 |
| 2o | 5033 | 4 | 78 | 9 | 84 | 89/11 |
| 2p | 5040 | 47 | 40 | 2 | 45 | 99/1 |
| 2q | 5041 | 13 | 42 | 1 | 36 | 73/27 |
| 2r | 5042 | 8 | 81 | 6 | 83 | >99/1 |
| 2s | 5043 | 4 | 82 | 9 | 80 | 99/1 |
| 2t | 5045 | 0.3 | 71 | 4 | 55 | 78/22 |
| 2u | 5046 | 1 | 76 | 17 | 75 | >99/1 |
| 2v | 5047 | 6 | 74 | 11 | 74 | 99/1 |
| 2w | 5048 | 2 | 74 | 16 | 72 | 96/4 |
| 2x | 5049 | 2 | 75 | 15 | 78 | 98/2 |
| 2y | 5050 | 0.2 | 74 | 16 | 72 | 95/5 |
| 2z | 5051 | 31 | 51 | 3 | 50 | 96/4 |

Reactions 2a-2q have been run in toluene distilled under argon, reactions 2r-2z have been run in toluene filtered through aluminum oxide (Fluka Catal. Nr. 06320)

Example 3

S/C 200

To a solution of 1.96 g (2.00 mmol) of diene IIb (as a 70% solution in toluene) in 156 mL of toluene was added under argon bubbling (33 mL/min) at 60° C. 8.49 mg (0.01 mmol) of catalyst 5001. After 5 h stirring at this temperature 50 µl (0.74 mmol) of ethylenediamine were added and the mixture was stirred at room temperature for 10 min. After this time the mixture was extracted with 1 M aqueous solution of hydrochloric acid and with water. Evaporation of the organic phase afforded 1.32 g of RCM-ester Ib with 73.4% purity (84% yield).

Example 4

S/C 135-200

The examples in Table 2 were carried out using the same procedure and conditions as in Example 3, but in the presence of various catalysts.

TABLE 2

| Reaction Nr. | Catalyst Nr. | RP column | | | Chiral column | |
|---|---|---|---|---|---|---|
| | | Diene IIb a % | RCM-Ester Ib a %/% y. | Dimers a % | RCM-Ester Ib a % | Epi-Ib a % |
| 4a | 5007 | 1 | 81/86 | 13.9 | 99.5 | 0.5 |
| 4b | 5008 | 0.3 | 80/87 | 15 | >99.8 | <0.2 |
| 4c | 5016 | 1 | 81/86 | 12.8 | 99.4 | 0.6 |
| 4d | 5003 | 2.5 | 80/84 | 11.8 | 99.4 | 0.6 |
| 4e | 5014 | 2 | 80/87 | 12.8 | >99.8 | <0.2 |
| 4f | 5028 | 2 | 81/81 | 12.3 | >99.8 | <0.2 |
| 4g | 5024 | 9 | 73/n.d. | 9 | >99.8 | <0.2 |

% y. = % yield determined by HPLC with internal standard;
a %: HPLC area %;
n.d.: not determined.
Reactions 4e-g: after 4 h, additional 0.005 mmol of catalyst were added, total reaction time was 6 h.

Example 5

The experiments in Table 3 have been carried out in analogy to Example 3 but at S/C of 400. Catalyst Nr. temperature, reaction time, yield and purity of RCM ester II are given in the table.

TABLE 3

| Reaction Nr. | Catalyst Nr. | T ° C. | RP column | | | Chiral column | |
|---|---|---|---|---|---|---|---|
| | | | Diene IIb a % (time) | RCM-Ester Ib a %/% y. | Dimers a % | RCM-Ester Ib a % | Epi-Ib a % |
| 5a | 5008 | 50 | 2 (5 h) | 77/n.d. | 13 | >99.8 | <0.2 |
| 5b | 5001 | 60 | 31 (6.5 h) | 53/n.d. | 8 | >99.8 | <0.2 |
| 5c | 5008 | 60 | 1 (4 h) | 82/85 | 13 | 99.7 | 0.3 |
| 5d | 5008 | 70 | 3.5 (4 h) | 80/87 | 11 | 99.8 | 0.2 |
| 5e | 5016 | 70 | 5 (7 h) | 78/83 | 10 | 99.5 | 0.5 |
| 5f | 5016 | 80 | 3 (3 h) | 82/83 | 10 | 99.7 | 0.3 |

% y = % yield determined by HPLC with internal standard;
a %: HPLC area %;
n.d.: not determined.

Example 6

S/C 1000, 60° C., Syringe Pump

To a solution of 19.90 g (15.00 mmol) of diene IIb (as a 51.6% solution in toluene) in 1.15 L of toluene was added under argon bubbling at 60° C. 14.2 mg (0.0149 mmol) of catalyst 5008 with a syringe pump during 1 h. After a total of 9 h 50 μl (0.74 mmol) of ethylene diamine were added and the mixture was left overnight at r.t. under argon. Then the mixture was concentrated under vacuum and washed with 1 M aqueous solution of hydrochloric acid. The organic phase was treated with charcoal. Filtration and evaporation to dryness afforded 10.0 g of RCM-ester Ib with 79.2% purity (80.4% yield).

Example 7

The experiments in Table 4 have been carried out in analogy to Example 6, Catalyst Nr., temperature, reaction time, yield and purity of RCM ester Ib are given in the table.

TABLE 4

| | | | | | RP column | | Chiral column | |
|---|---|---|---|---|---|---|---|---|
| Reaction Nr. | Catalyst Nr. | T ° C. | Addn. time | Diene IIb a % (time) | RCM-Ester Ib a %/% y. | Dimers a % | RCM-Ester Ib a % | Epi-Ib a % |
| 7a | 5008 | 70 | 1 h | 3 (5 h) | 80/81 | 11.4 | >99.8 | <0.2 |
| 7b | 5008 | 70 | 1.5 h | 3 (2.5 h) | 81/82 | 11.1 | >99.8 | <0.2 |
| 7c | 5008 | 70 | $ | 4 (6 h) | 80/81 | 10.6 | >99.8 | <0.2 |
| 7d | 5016 | 80 | 1.5 h | 2 (2.5 h) | 82/84 | 11.2 | >99.8 | <0.2 |
| 7e | 5001 | 70 | 1.5 h | 2 (2.5 h) | 80/82 | 13.0 | >99.8 | <0.2 |

% y = % yield determined by HPLC with internal standard;
a %: HPLC area %
Reaction Nr. 7d and 7e have been carried out at S/C of 600.
$ Catalyst was added in one portion at beginning of reaction.

Example 8

S/C 1000, Vacuum, P=0.26 bar

To a solution of 6.25 g (5.00 mmol) of diene IIb (as a 54.8% solution in toluene) in 380 mL of toluene was added at 70° C. under vacuum (pressure=ca. 0.26 bar) by dropping funnel a solution of 4.26 mg (0.005 mmol) of catalyst 5001 in 21 mL of toluene. The catalyst was added during 1.5 h. Under these conditions a small amount of toluene (14 mL) distilled off in the course of the reaction. After 2 h of total reaction time 22 μL (0.326 mmol) of ethylene diamine were added at ambient pressure, the reaction mixture was concentrated under vacuum, washed with 0.5 M aqueous solution of hydrochloric acid and evaporated to dryness. RCM-ester Ib was isolated as a light brown solid (3.97 g) with 72.3% purity (87.4% yield). Crystallization from toluene/diethyl ether afforded RCM-ester Ib as white crystals with 96.3% purity (HPLC), m.p. 110-113° C.

Example 9

The experiments in Table 5 have been carried out in analogy to Example 8, Catalyst Nr., temperature, reaction time, yield and purity of RCM ester Ib are given in the table.

TABLE 5

| | | | | RP column | | Chiral column | |
|---|---|---|---|---|---|---|---|
| Reaction Nr. | Catalyst Nr. | T ° C. | Diene IIb a % (time) | RCM-Ester Ib a %/% y. | Dimers a % | RCM-Ester Ib a % | Epi-Ib a % |
| 9a | 5008 | 70 | 0.4 (2 h) | 82/84 | 13.4 | >99.8 | <0.2 |
| 9b | 5001 | 70 | 1.0 (2 h) | 82/87 | 12.8 | >99.8 | <0.2 |
| 9c | 5016 | 80 | 1.0 (2 h) | 83/82 | 11.8 | >99.8 | <0.2 |
| 9d | 5028 | 70 | 0.8 (2 h) | 82/84 | 12.6 | >99.8 | <0.2 |
| 9e | 5048 | 70 | 0.6 (1.5 h) | 83 87 | 12.8 | >99.8 | <0.2 |
| 9f | 5049 | 70 | 1.3 (2 h) | 80/86 | 12.0 | >99.8 | <0.2 |
| 9g | 5050 | 70 | 0.8 (2 h) | 83/87 | 12.4 | >99.8 | <0.2 |

All reactions were run at S/C 1000. Reaction 9a was run on a 10 mmol scale.
% y = % yield determined by HPLC with internal standard;
a %: HPLC area %

Example 10

S/C 2000, Vacuum, P=0.26 bar

Example 10 was carried out in analogy to example 8, but 2.3 mg of catalyst 5008 were added over 1 h. After 2 h of total reaction time, work-up as in example 8 with final charcoal treatment afforded after evaporation of the solvent RCM-ester Ib as an off-white solid (3.48 g) with 78% purity (83.1% yield)

Example 11

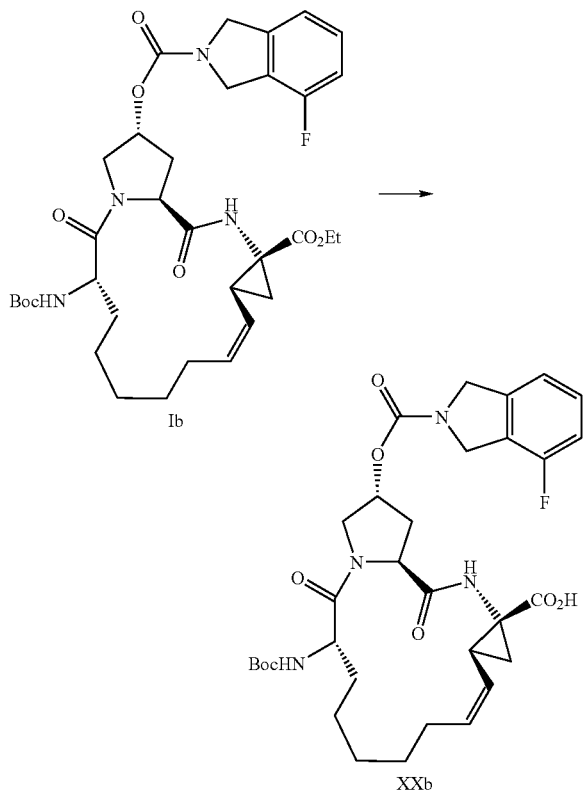

Preparation of (2R,6S,12Z,13aS,14aR,16aS)-6-[[(tert-butoxy) carbonyl]amino]-2-[[(4-fluoro-1,3-dihydro-2H-isoindol-2-yl)carbonyl]oxy]-1,2,3,6,7,8,9,10,11,13a,14,15,16,16a-hexadecahydro-5,16-dioxo]-cyclopropa[e]pyrrolo[1,2-a][1,4]diaza-cyclopentadecine-14a(5H)-carboxylic acid.

To a solution of 59.7 g (90.9 mmol) of RCM-ester Ib in 350 g of ethanol at 7° C. was added over one hour 231 g of a sodium hydroxide solution (20% in water) and the resulting mixture was stirred for 6 hours at 5-10° C. The mixture was then treated at 10° C. with 110 g of concentrated hydrochloric acid (37%). From the resulting mixture (approx. 800 mL) ethanol/water was distilled off until a residual volume of 350-400 mL was obtained in the reactor. The residue was treated at 40° C. with 320 g of dichloromethane and 55 g of water and the resulting biphasic mixture was stirred at 40° C. for 20 minutes. Stirring was stopped and the layers were allowed to separate for 15 minutes. The lower organic layer was separated. The aqueous layer was extracted with 64 g of dichloromethane and the combined organic layers were washed with water (1×55 g). dichloromethane was distilled From the organic layer at atmospheric pressure and the removed solvent was continuously replaced by tetrahydrofuran; whereby the product crystallized out. In total, 600 g of tetrahydrofuran have been added. At the end of the distillation a volume of approx. 700 mL was adjusted in the reactor. After the distillation the suspension was heated to reflux for 5 hours. The suspension was then cooled to 0° C. within 2 hours and stirred at this temperature for additional 3 hours. The crystals were filtered off, washed with 95 g of tetrahydrofuran and dried at 50° C./<30 mbar for 10 hours to afford 55.20 g (87% corrected yield) of the title compound as white crystals with a purity of 98.4%(area), an assay of 90.2%(m/m) and a THF content of 8.5%.

MS: 627.3 ($M^+$–H).

$^1$H-NMR (400 MHz, DMSO-$d_6$): 12.2 (s, 1H), 8.73-8.66 (m, 1H), 7.39-7.31 (m, 1H), 7.22-7.02 (m, 3H), 5.57-5.46 (m, 1H), 5.31-5.21 (m, 2H), 4.67 (s, br, 4H), 4.47-4.38 (m, 1H), 4.29-4.20 (m, 1H), 3.98-3.88 (m, 1H), 3.71-3.62 (m, 1H), 2.70-2.55 (m, 1H), 2.29-2.08 (m, 3H), 1.75-1.0 (m, 11H), 1.10 and 1.07 (2s, 9H).

Example 12

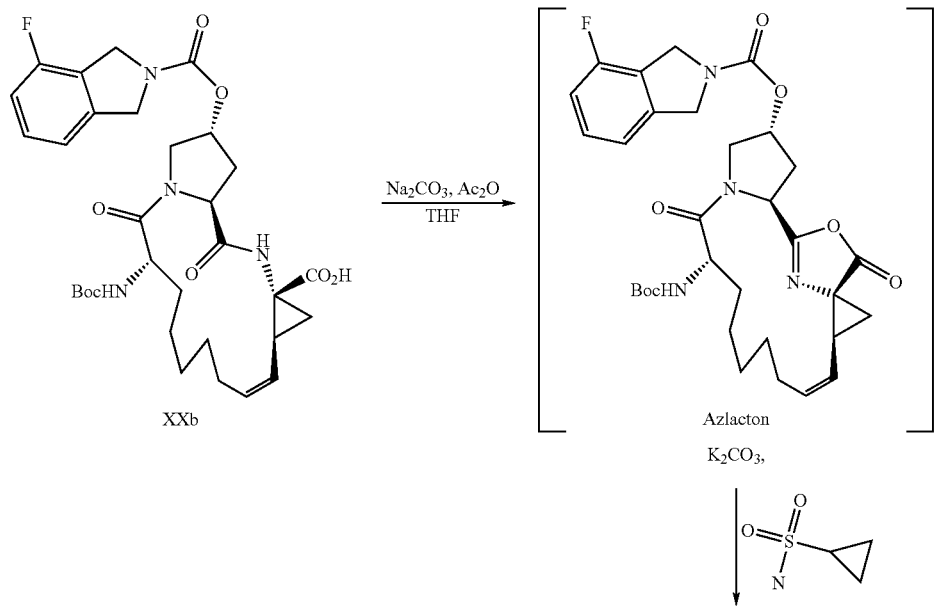

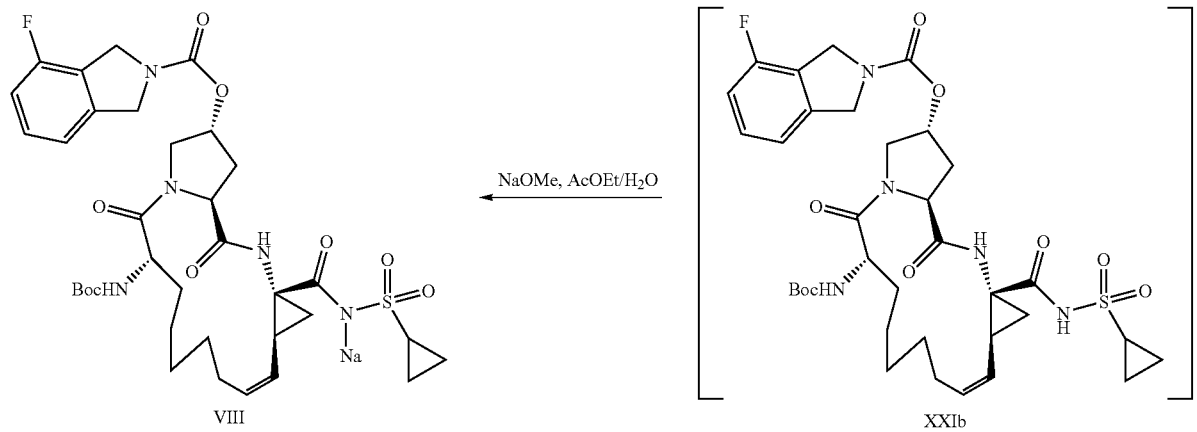

Preparation of Sodium ((2R,6S,13aS,14aR,16aS,Z)-6-(tert-butoxycarbonylamino)-2-(4-fluoroisoindoline-2-carbonyloxy)-5,16-dioxo-1,2,3,5,6,7,8,9,10,11,13a,15,16a-hexadecahydrocyclopropa[e]pyrrolo[1,2-a][1,4]diazacyclopentadecine-14a-carbonyl) (cyclopropylsulfonyl) amide (HCV protease inhibitor; compound VIII)

To a suspension of 30.0 g (0.043 mol) of XXb from example 11 with an assay of 90.2%(m/m)) and 14.0 g of sodium carbonate in 225 g of tetrahydrofuran was added at 45° C. within 30 minutes 7.60 g (0.074 mol) of acetic acid anhydride and the resulting mixture was stirred at 45° C. for 8 hours. To the resulting suspension was then added 30.2 g (0.17 mol) of potassium carbonate and 8.0 g (0.065 mol) of cyclopropyl sulfonamide. The mixture was heated to 62° C. and stirred at this temperature for 17 hours. The mixture was concentrated to a residual volume of 200 mL and then treated with 200 g of water. The biphasic mixture was stirred for 15 minutes and the layers were then allowed to separate. The lower aqueous phase was removed. The organic phase was diluted with 90 g of ethyl acetate and washed with 3% sulfuric acid (1×140 g) and water (3×130 g). The organic layer was concentrated to dryness and then redissolved in 400 mL of ethyl acetate. Residual amounts of water were removed by a continuous azeotropic distillation with ethyl acetate. The mixture was then treated at 10° C. with 20 mL of methanol, followed by 10.0 g of sodium methylate (30% in methanol). From the resulting mixture approx. 300 mL of ethyl acetate/methanol were then distilled off. The mixture was then treated at 34° C. within one hour with 300 mL of ethyl acetate and 5 g of water. The resulting mixture was allowed to cool to ambient temperature within 4 hours. The crystals were filtered off, washed with 80 mL of ethyl acetate and dried at 80° C./<30 mbar for 20 hours to afford 30.4 g (87% corrected yield) of the title compound as white crystals with an assay of 92.7%(m/m).

MS: 732.28 (M$^+$+H), 676.23, 632.25.

$^1$H-NMR (400 MHz, DMSO-d$_6$): 7.89-7.80 (m, 1H), 7.39-7.31 (m, 1H), 7.21-7.06 (m, 2H), 6.97-6.90 (m, 1H), 5.49-4.41 (m, 1H), 5.31-5.21 (m, 2H), 4.66 (s, br, 4H), 4.45-4.35 (m, 1H), 4.19-4.08 (m, 2H), 3.91-3.81 (m, 1H), 2.68-2.58 (m, 1H), 2.30-2.14 (m, 3H), 2.0-1.2 (m, 12H), 1.17 and 1.14 (2s, 9H), 0.78-0.69 (m, 2H), 0.62-0.53 (m, 2H).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A process for the manufacture of a macrocyclic compound of

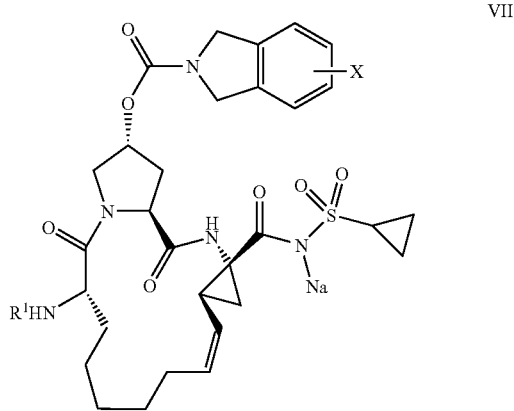

VII formula VII comprising the steps of:

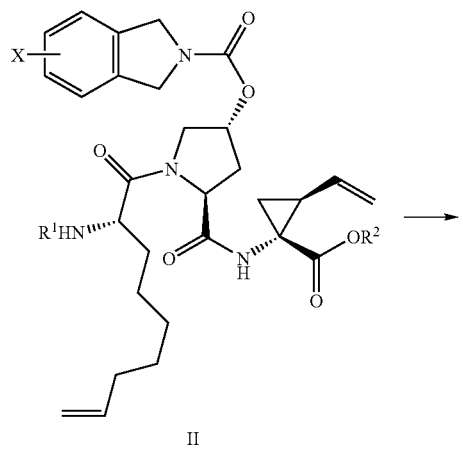

II

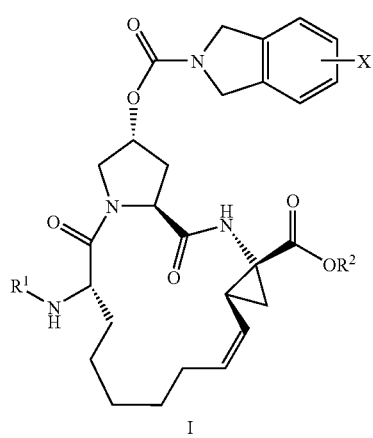

I

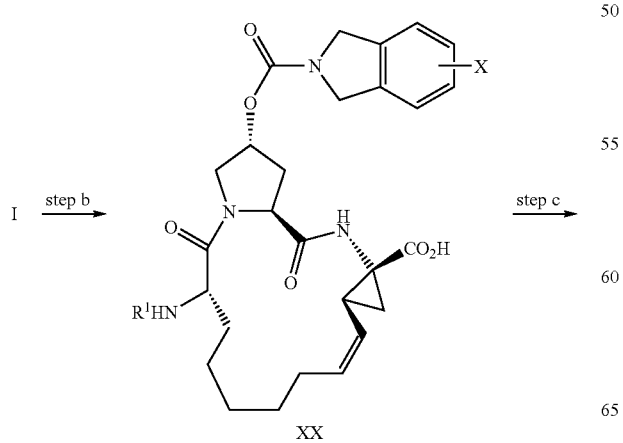

XX

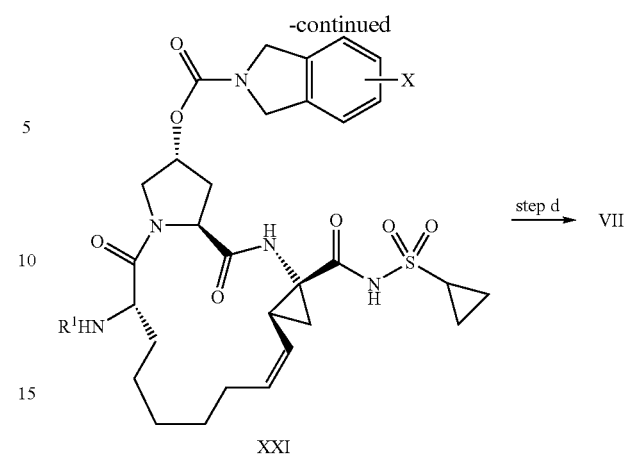

XXI b) hydrolyzing the macrocyclic ester of formula I in the presence of a base to form a macrocyclic acid of the formula XX wherein $R^1$ is an amino protecting group and X is halogen;
c) coupling the macrocyclic acid of formula XX with cyclopropyl sulfonamide to form a macrocyclic sulfonamide of formula; and,
d) treating the macrocyclic sulfonamide of formula XXI with a sodium base to form a macrocyclic compound of formula VII.

2. A process according to claim 1 wherein the pentacoordinated ruthenium (II) carbene complex catalyst is selected from compounds of the formula III to V wherein

III

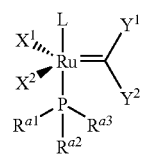

IV

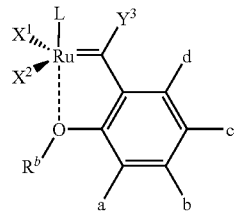

V

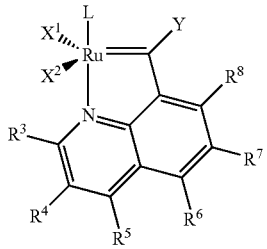

(a) contacting a diene of formula II wherein $R^1$ is an amino protecting group and X is a halogen atom, with a pentacoordinated ruthenium (II) carbene complex ring-closing catalyst to form a macrocyclic ester of formula I wherein $R^1$ is an amino protecting group, $R^2$ is $C_{1-4}$-alkyl and X is halogen;

L is a neutral ligand;
$X^1$ and $X^2$ independently of each other are anionic ligands;
Y is hydrogen, $C_{1-6}$-alkyl, $C_{2-6}$-alkenyl or aryl, or Y and $R^8$ taken together to form a (CH=CR)— or a —$(CH_2)_n$— bridge wherein n is 2 or 3 and R is as defined for $R^4$;
$Y^1$ and $Y^2$ are independently hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl, or $Y^1$ and $Y^2$ taken together are VIa

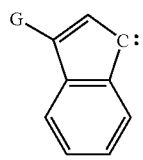

VIa wherein G is hydrogen or aryl; or, $Y^1$ and $Y^2$ together form a cumulenyl group VIb or VIc

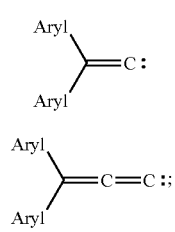

VIb

VIc $Y^3$ is hydrogen, $C_{1-6}$-alkyl, $C_{2-6}$-alkenyl, $C_{2-6}$-alkynyl, $C_{1-6}$-alkylthio, aryl, arylthio, $C_{1-6}$-alkylsulfonyl or $C_{1-6}$-alkylsulfinyl;

$R^{a1}$, $R^{a2}$ and $R^{a3}$ independently of each other are $C_{1-6}$-alkyl, $C_{3-7}$-cycloalkyl, aryl or heteroaryl or $R^{a1}$ and $R^{a2}$ or $R^{a2}$ and $R^{a3}$ or $R^{a1}$ and $R^{a3}$ form together a 1,5-bridged cyclooctyl group;

$R^b$ is $C_{1-6}$-alkyl $C_{2-6}$-alkenyl, halogen-$C_{1-6}$-alkyl, $C_{2-6}$-alkynyl, aryl, $C_{1-6}$-alkoxycarbonyl, $C_{1-6}$-alkylcarbonyl, mono-$C_{1-6}$-alkyl- or di-$C_{1-6}$-alkylamino, $C_{1-6}$-alkylaminocarbonyl, $C_{1-6}$-alkylthiocarbonyl, $C_{1-6}$-alkylsulfonyl, $C_{1-6}$-alkylsulfinyl or arylalkyl;

$R^3$, $R^4$, $R^5$, $R^6$, $R^7$ and $R^8$ are independently hydrogen, $C_{1-6}$-alkyl, halogen-$C_{1-6}$-alkyl, $C_{2-6}$-alkenyl, $C_{2-6}$-alkynyl, halogen-$C_{1-6}$-alkyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfonyl, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl or $OSi(C_{1-6}$-alkyl$)_3$ or $SO_2$—NR'R" wherein R' and R" independently are hydrogen, aryl or $C_{1-6}$-alkyl or R' and R" together with the N atom are a carbocycle;

a, b, c and d are independently hydrogen, $C_{1-6}$-alkyl, halogen-$C_{1-6}$-alkyl, $C_{2-6}$-alkenyl, $C_{2-6}$-alkynyl, halogen-$C_{1-6}$-alkyl, $C_{1-6}$-alkoxy, $C_{2-6}$-alkenyloxy, $C_{2-6}$-alkynyloxy, $C_{1-6}$-alkylcarbonyl, aryl, hydroxy, aryloxy, nitro, $C_{1-6}$-alkoxycarbonyl, amino, mono-$C_{1-6}$-alkyl- or di-$C_{1-6}$-alkylamino, halogen, thio, $C_{1-6}$-alkylthio, arylthio, $C_{1-6}$-alkylsulfinyl, arylsulfonyl, $SO_3H$, $C_{1-6}$-alkylcarbonyl amino, aryl carbonyl amino, $C_{1-6}$-alkyl sulfonyl amino, aryl sulfonyl amino, halogen-$C_{1-6}$-alkyl sulfonyl amino, $SO_3$—$C_{1-6}$-alkyl $OSi(C_{1-6}$-alkyl$)_3$ or $SO_2$—NR'R" wherein R' and R" independently are hydrogen, aryl or $C_{1-6}$-alkyl or R' and R" together with the N atom are a carbocycle.

3. A process according to claim 2 wherein L is —$P(R^{a1})(R^{a2})(R^{a3})$;

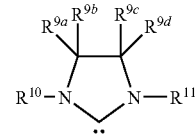

VII

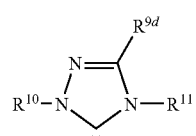

VIII

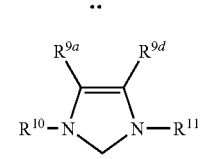

IX wherein $R^{10}$ and $R^{11}$ are independently $C_{1-6}$-alkyl, aryl, $C_{2-6}$-alkenyl or 1-adamantyl and $R^{9a-d}$ are independently hydrogen, $C_{1-6}$-alkyl, $C_{2-6}$-alkenyl or aryl, or, $R^{9b}$ and $R^{9c}$ or $R^{9a}$ and $R^{9d}$ taken together form a-$(CH_2)_4$-bridge;

$R^{a1-a3}$ are independently $C_{1-6}$-alkyl, $C_{3-7}$-cycloalkyl, aryl or heteroaryl, or $R^{a1}$ and $R^{a2}$ or $R^{a2}$ and $R^{a3}$ or $R^{a1}$ and a3 form together a 1,5-bridged cyclooctyl group.

4. A process according to claim 2 wherein $X^1$ and $X^2$ are a halogen or a pseudo halogen.

5. A process according to claim 2 wherein:

Y is hydrogen;

$Y^1$ and $Y^2$ are the same or different and stand for hydrogen, $C_{1-6}$-alkyl, $C_{2-6}$-alkenyl, $C_{1-6}$-alkylthio, phenyl or phenylthio, or $Y^1$ and $Y^2$ taken together form a cycle VI wherein is hydrogen or phenyl;

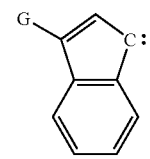

VI $Y^3$ is hydrogen.

6. A process according to claim 2 wherein $R^b$ is $C_{1-6}$-alkyl and halogen-$C_{1-6}$-alkyl;

a, b and d are hydrogen; and, c is hydrogen, halogen, nitro, $C_{1-6}$-alkylcarbonyl amino, aryl carbonyl amino, aryl sulfonyl amino, alkyl sulfonyl amino, halogen-$C_{1-6}$-alkyl sulfonyl amino or $SO_2NR'R"$ wherein R' and R" independently are of hydrogen, $C_{1-6}$-alkyl or aryl, or, R' and R" together with the N atom are a carbocycle.

7. A process according to claim 2 wherein the ring closing metathesis reaction in step a) is performed in an organic solvent at 20° C. to 140° C.

8. A process according to claim 2 wherein the ring closing metathesis reaction in step a) is performed with a substrate to catalyst ratio in then range of 20 to 10000.

9. A process according to claim 1 wherein the hydrolysis in step b) to afford XX is performed with an aqueous alkali hydroxide solution at a temperature of 0° C. to 40° C.

10. A process according to claim 9 wherein in that the macrocyclic acid of formula XX obtained in step b) is isolated by extraction with dichloromethane and a subsequent crystallization in tetrahydrofuran.

11. A process according to claim 1 which process further comprises the step of treating XX with acetic acid anhydride in the presence of an inorganic base and a suitable organic solvent to afford an azlactone intermediate of the formula XXIII which is

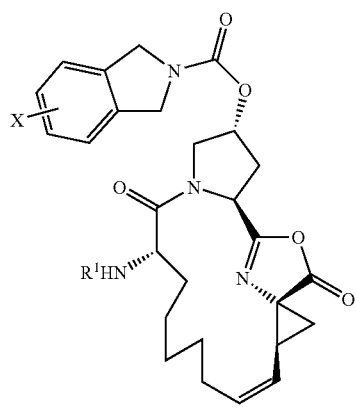

XXIII subsequently converted into formula XXI wherein: $R^1$ is an amino protecting group and X is halogen.

12. A process according to claim 1 wherein the sodium base used to convert the macrocyclic sulfonamide of the formula XXI in step d) into a salt is sodium hydroxide, sodium methylate or sodium ethoxide.

13. A process according to claim 2 wherein $R^1$ is Boc;

$R^2$ is ethyl;

and the moiety of the formula

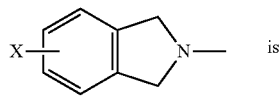 is

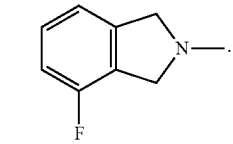.

* * * * *